United States Patent
Shokoohi (10) Patent No.: US 8,945,201 B2
(45) Date of Patent: Feb. 3, 2015

(54) PROSTHESIS DELIVERY SYSTEM

(71) Applicant: Telesis Research, LLC, Coral Gables, FL (US)

(72) Inventor: Mehrdad M. Shokoohi, Miami, FL (US)

(73) Assignee: Telesis Research, LLC, Coral Gables, FL (US)

( * ) Notice: Subject to any disclaimer, the term of this patent is extended or adjusted under 35 U.S.C. 154(b) by 250 days.

(21) Appl. No.: 13/754,811

(22) Filed: Jan. 30, 2013

(65) Prior Publication Data
US 2014/0214148 A1    Jul. 31, 2014

(51) Int. Cl.
*A61F 2/06* (2013.01)
*A61F 2/95* (2013.01)

(52) U.S. Cl.
CPC .................................. *A61F 2/95* (2013.01)
USPC .................................................. 623/1.12

(58) Field of Classification Search
USPC ................ 623/1.11, 1.12, 1.23; 606/108, 200
See application file for complete search history.

(56) References Cited

U.S. PATENT DOCUMENTS

| | | | |
|---|---|---|---|
| 6,113,622 A * | 9/2000 | Hieshima | 606/200 |
| 6,171,327 B1 * | 1/2001 | Daniel et al. | 606/200 |
| 8,753,384 B2 * | 6/2014 | Leanna | 623/1.11 |
| 2003/0004537 A1 * | 1/2003 | Boyle et al. | 606/200 |
| 2003/0114879 A1 * | 6/2003 | Euteneuer et al. | 606/200 |
| 2003/0225445 A1 * | 12/2003 | Derus et al. | 623/1.11 |
| 2003/0236533 A1 * | 12/2003 | Wilson et al. | 606/127 |
| 2005/0149110 A1 * | 7/2005 | Wholey et al. | 606/200 |
| 2005/0159773 A1 * | 7/2005 | Broome et al. | 606/200 |
| 2005/0177185 A1 * | 8/2005 | Becker et al. | 606/200 |
| 2005/0222604 A1 * | 10/2005 | Schaeffer | 606/200 |
| 2007/0060944 A1 * | 3/2007 | Boldenow et al. | 606/200 |
| 2007/0270937 A1 * | 11/2007 | Leanna | 623/1.12 |
| 2012/0041474 A1 * | 2/2012 | Eckhouse et al. | 606/200 |
| 2012/0130418 A1 * | 5/2012 | Jenson et al. | 606/200 |

* cited by examiner

*Primary Examiner* — Jonathan W Miles
(74) *Attorney, Agent, or Firm* — Knobbe, Martens, Olson & Bear, LLP (57) ABSTRACT

Disclosed herein are implantable, radially expandable medical prostheses, including but not limited to stents, and delivery and loading systems applicable to the same, including disposable, detachable distal chambers, and methods for using the same.

32 Claims, 12 Drawing Sheets

PROSTHESIS DELIVERY SYSTEM

BACKGROUND

Field of the Invention

The present invention relates generally to implantable, radially expandable medical prostheses, including but not limited to stents, and delivery and loading systems applicable to the same.

SUMMARY OF THE INVENTION

Disclosed herein are various prosthesis delivery systems, and methods of using the same. The system can comprise an elongate tubular body having a proximal end, tubular body, distal end, and a central lumen therethrough. The distal end can comprise a chamber detachable from the remainder of the elongate tubular body, the distal chamber having a first rigid distal segment and a second flexible proximal transition segment, the first distal segment having an inner diameter, the inner diameter of the first distal segment being substantially constant and configured to house therethrough a prosthesis in a less than fully compressed configuration, the second proximal transition segment having an inner diameter that generally decreases from the distal end to the proximal end of the transition segment, the second proximal transition segment having an axial length that is at least 1.5×, 2×, 2.5×, 3×, 4×, 5×, 6×, or more with respect to the inner diameter or the outer diameter of the first distal segment. The tubular body can have an inner diameter smaller than the inner diameter of the first distal segment of the chamber. The system can also include a retrieval element configured to move the prosthesis proximally from the chamber, through the transition segment into the tubular body, thereby transforming the prosthesis from the less than fully compressed configuration when stored in the chamber to a fully compressed configuration.

In some embodiments, the inner diameter of the second proximal transition segment gradually decreases from its distal end to its proximal end. At least a portion of a sidewall defining the inner diameter of the first distal segment of the distal chamber can comprise an inner diameter wall surface treatment to change, such as decrease the coefficient of friction relative to an untreated surface. The surface treatment could include, for example, a corona treatment, a coating, hydrophilic treatment, hydrophobic treatment, or others. The distal chamber can comprise an element selected from the group consisting of: a radioactive element, a drug, a stem cell, and a bioactive agent. The retrieval element can be removably attached to the prosthesis such as, for example, a control wire, suture, or clamp, or alternatively remote from the prosthesis such as a vacuum or pressure source. The retrieval element can be detachable from the tubular body in a number of ways, including a compression/friction fit. The system can include one, two, or more expandable elements, such as balloons proximate the distal end of the tubular body, and can also include a plurality of radiopaque marker elements positioned on the proximal end and a distal end of the balloon. At least a portion of the distal chamber can have a see-through portion configured to allow an operator to visually gauge the position of the prosthesis within the delivery system. The tubular body can comprise at least one fluid delivery port near the proximal end of the tubular body, and a guidewire configured to reside within the central lumen of the elongate tubular body. The chamber could be reusable or disposable. The chamber could comprise a first flange removably attached to a second flange of the tubular body. The first flange and the second flange can be angled with respect to a long axis of the chamber and a long axis of the tubular body. An inner or outer surface of the first flange can contact a respective inner or outer surface of the second flange.

In some embodiments, a medical system could include a prosthesis delivery system such as disclosed herein, as well as one, two, or more prostheses. The prostheses could be, for example, self-expanding or balloon expandable stents, such as carotid, coronary, or peripheral stents.

Also disclosed herein is a method of delivering an expandable prosthesis, comprising providing a prosthesis delivery system having a detachable, disposable distal chamber removably attached at its proximal end to the distal end of a tubular body; wherein the expandable prosthesis is stored in a first, relatively expanded state within the chamber; and transferring the expandable prosthesis from the chamber to the tubular body by using vacuum or pressure to move the expandable prosthesis proximally, transforming the prosthesis from the first relatively expanded state to a second relatively compressed state during the transfer.

Also disclosed herein is a method of delivering an expandable prosthesis, comprising: providing a prosthesis delivery system having a detachable, disposable distal chamber removably attached at its proximal end to the distal end of a tubular body, the chamber having a proximal transition segment and a distal segment having a substantially constant outer diameter, the transition segment having a proximal end and a distal end, the transition segment having an axial length, a first inner diameter at the proximal end and a second inner diameter at the distal end, the transition segment having a first inner diameter that is less than the second inner diameter of the transition segment, the transition segment having an axial length that is at least about 2× the outer diameter of the distal segment, wherein the expandable prosthesis is stored in a first, relatively expanded state within the chamber; and transferring the expandable prosthesis from the chamber to the tubular body to move the expandable prosthesis proximally, transforming the prosthesis from the first relatively expanded state to a second relatively compressed state during the transfer.

Transferring the prosthesis from the chamber to the tubular body could be performed using vacuum and/or pressure, or by moving a control wire removably connected to the prosthesis in a proximal direction. The method could also include delivering the prosthesis to a stenosis within a lumen of the body, and expanding the prosthesis to dilate the stenosis.

DETAILED DESCRIPTION

The present invention relates generally to systems and methods for deploying prostheses, such as stents or stent-grafts, at one or more treatment sites. In some embodiments, disclosed herein is a sterilizable, disposable, intraluminal medical device delivery system having a partially or completely clear, rigid, detachable, disposable, distal chamber (DDDC) with a rigid distal section of the tip and flexible shaft and having one, two, or more lumens that can serve, for example, as guidewire and/or fluid injection ports.

A delivery device for application/implantations of different forms of implantable medical devices for treatment, e.g., of coronary and peripheral vascular disease including stents, stent-grafts, bioactive devices, radioactive devices, drug-coated devices, devices incorporating stem cells, gene therapy, and multi-layered eluting prostheses may include various shapes such as generally flat sheets, a cylindrical or conical shape, and many other forms and geometries including but not limited to concave and convex forms. Such devices have become an increasingly important treatment option for patients with a body lumen stenosis, such as one involving the vasculature. Some examples include coronary artery disease, cerebrovascular disease, carotid stenosis, and peripheral vascular disease, among others. Stenting involves the placement of a tubular prosthesis within a diseased lumen, such as an artery to expand the lumen and maintain the patency of the vessel. Early stent technology suffered from problems with restenosis, the tendency of the artery to become re-occluded following stent placement. However, improvements in stent design and the advent of drug-eluting stents have reduced restenosis rates dramatically. As a result, the number of stenting procedures being performed in the United States, Europe, and elsewhere has soared.

Prostheses, including stents and stent-grafts are delivered to the target lumen, such as the coronary or peripheral arteries using long, flexible vascular catheters typically inserted through a femoral artery, brachial artery, or other access point. For self-expanding stents, the stent is simply released from the delivery catheter and it resiliently expands into engagement with the vessel wall. For balloon expandable stents, a balloon on the delivery catheter is expanded which expands and deforms the stent to the desired diameter, whereupon the balloon is deflated and removed. For certain self-expanding stents, a touch-up utilizing a balloon can ensure that the stent is appropriately radially expanded in the desired location within the body.

There are various prostheses for implantation in blood vessels or other similar organs of the living body. For example, "self-expanding" stents are stents inserted into the vascular system in a radially compressed or contracted state, and permitted to expand upon removal of a restraint. Self-expanding stents typically employ a wire or tube configured (e.g., bent or cut) to provide an outward radial force and employ a suitable elastic material such as stainless steel or Nitinol (nickel-titanium). Nitinol may additionally employ shape memory properties. In some embodiments, stents can have biodegradable properties.

A self-expanding implantable drug eluting prosthesis, in some embodiments, can be sized to be configured in a tubular shape of a slightly greater diameter than the diameter of the blood vessel in which the stent is intended to be used. In general, stents are typically deployed using a minimally invasive intraluminal delivery, e.g., cutting through the skin to access a lumen or vasculature or percutaneously via successive dilatation, at a convenient (and less traumatic) entry point, and routing the stent through the lumen to the site where the prosthesis is to be deployed. Intraluminal deployment in one example is effected using a delivery catheter with a coaxial inner tube, sometimes called the plunger, and sheath, arranged for relative axial movement. The stent is compressed and disposed within the distal end of the sheath in front of the inner tube.

The catheter is then maneuvered, typically routed though a lumen (e.g., vessel), until the end of the catheter (and the stent) is positioned in the vicinity of the intended treatment site. The inner tube is then held stationary while the sheath of the delivery catheter is withdrawn. The inner tube prevents the stent from moving back as the sheath is withdrawn. As the sheath is withdrawn, the stent is gradually exposed from a distal end to a proximal end of the stent, the exposed portion of the stent radially expands so that at least a portion of the expanded portion is in substantially conforming surface contact with a portion of the interior of the lumen, e.g., the blood vessel wall.

Lesions in the peripheral vasculature are sometimes considerably longer than those in the coronary arteries. To accommodate the greater length of the lesion, long stents can be used, e.g., 150 mm or greater length stents.

In some embodiments, prostheses including stents and stent-grafts can advantageously be loaded into delivery tools before arrival to the operating suite, and thus can store a stent in an expanded state until ready for placement, at which point the system permits the stent to be compressed and transferred into a delivery tool. In some embodiments, the delivery systems include a delivery tool including a tubular body and a distal detachable or non-detachable chamber, wherein the prosthesis is stored in the distal chamber in an expanded state. The prosthesis can be transferred to the delivery tool on-site and immediately prior to the delivery and deployment procedure. Among the advantages of such a delivery system is that stress relaxation and/or creep of the prosthesis is minimized. This could be particularly advantageous for polymeric stents which may exhibit substantial stress relaxation and creep if stored in a compressed state over a long period of time. Furthermore, the likelihood of contaminating the stent during the loading procedure is reduced because the prosthesis is enclosed in the distal chamber before and during the loading procedure.

Figure 1:
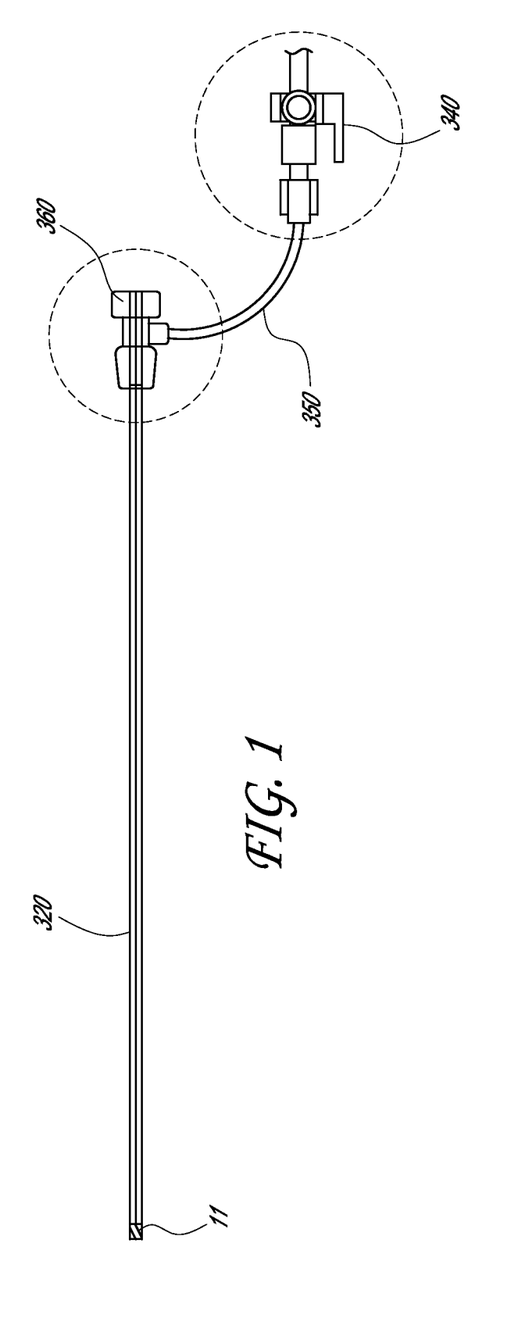
FIGS. 1-3 illustrate schematically features of a coaxial stent delivery system according to some embodiments of the invention.
Figure 2:
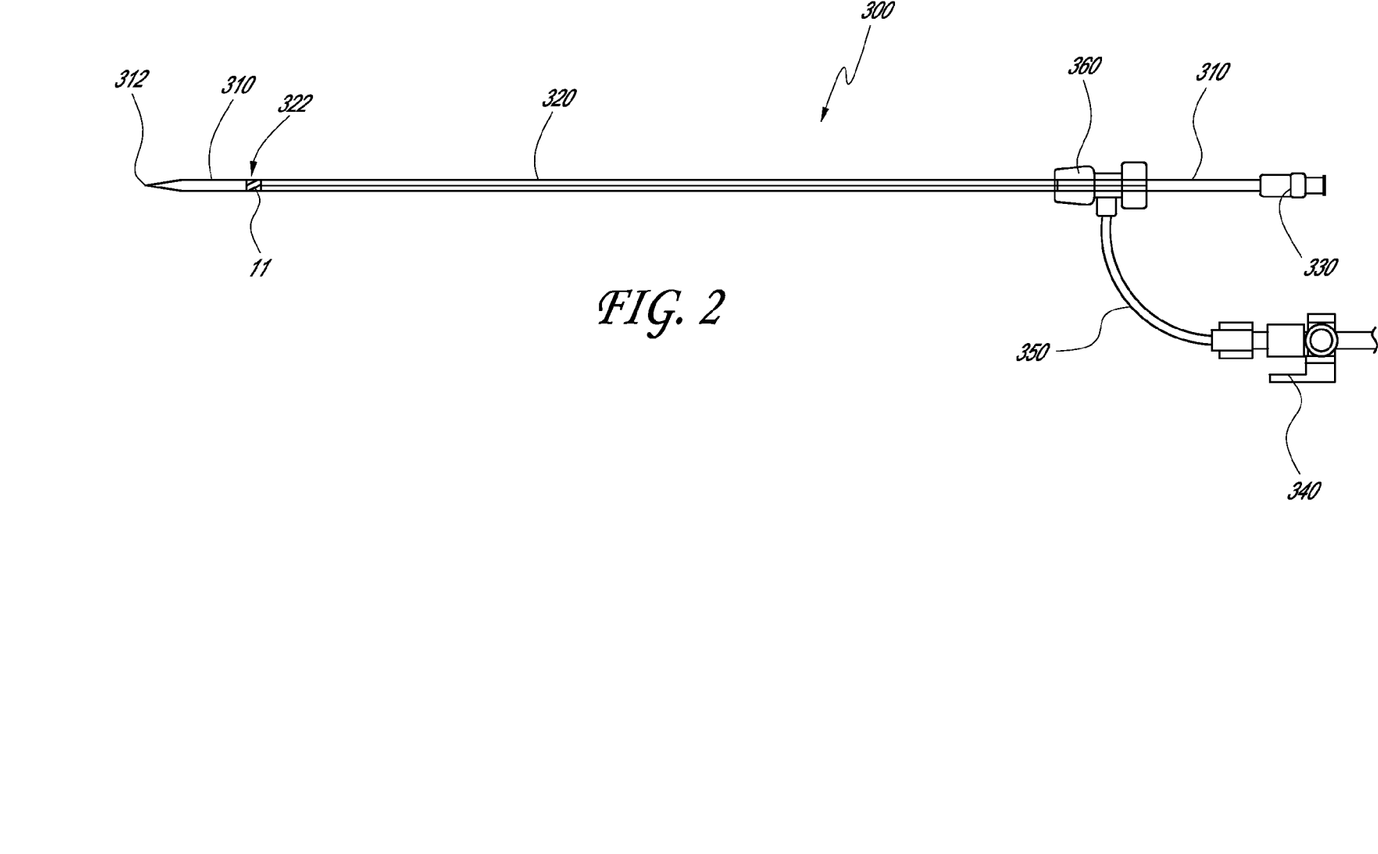
Figure 3:
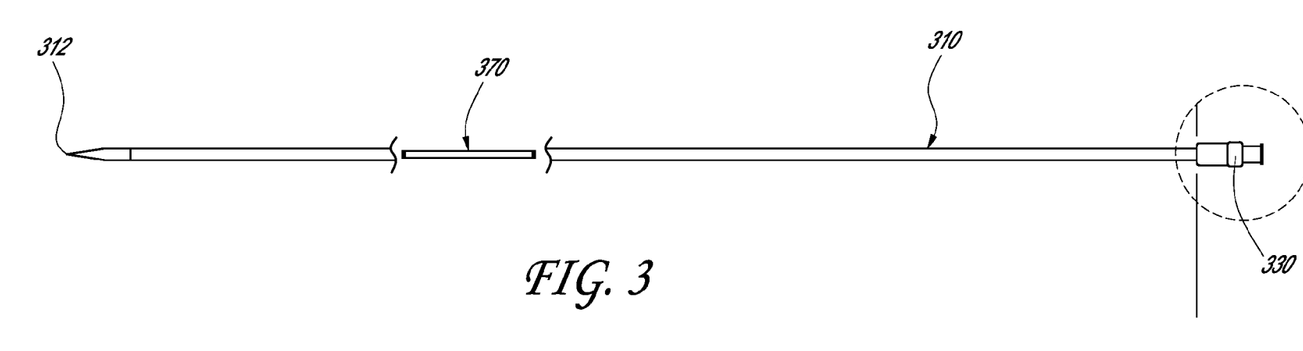

FIG. 1 illustrates features of a prostheses delivery system 300 including an inner tube 310 having a proximal end and a distal end which comprises a distal tip 312, and an outer tube 320 having a proximal end and a distal end 322 configured to slide coaxially over the inner tube 310. In some embodiments, an outer sheath is included over the outer tube 320 and can function as an introducer. A radioopaque marker 11 can be positioned at or near the distal end 322 of the outer tube 320 as illustrated. Radiopaque markers are used to visualize the position of the stent 160 through fluoroscopy during implantation. In some embodiments, a radiopaque marker 11 can also be placed at or near the distal end 312 of the inner tube 310 as well. In such embodiments with a marker 11 on both the inner tube 310 and the outer tube 320, movement, such as proximal retraction of the inner tube 310 by a distance greater than the length of the stent 160 can serve as an indicator that the stent 160 should expand and be deployed in the desired vessel. Also shown is a proximal Luer port 330 adapted to house a guidewire therethrough and/or for infusion or aspiration of fluid, medication, or the like via the inner tube 310 lumen. The proximal end of the outer tube 320 includes a proximal adapter 360 connected via tubing 350 to a check valve 340 for infusion or aspiration of fluid, medication, or the like via the outer tube 320 lumen. FIG. 2 is a schematic view of the outer tube 320 with components as previously described. FIG. 3 is a schematic view of the inner tube 310 with components as previously described, also including a hypotube 370 within inner tube 310. In some embodiments, the delivery system or components thereof could have an outer diameter of between about 5 and 16 French, such as between about 6 and 15 French.

Figure 4:
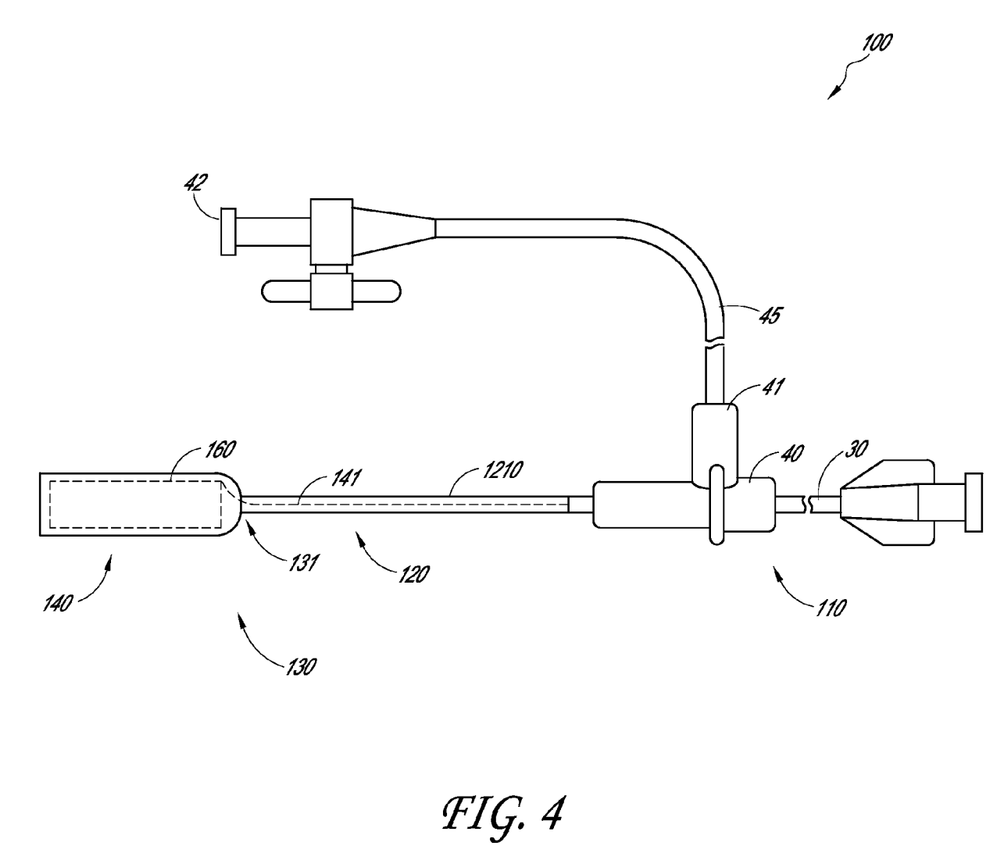
FIG. 4 illustrates schematically a coaxial stent delivery system that includes a distal detachable chamber and a stent retraction feature, according to some embodiments of the invention.

Referring to FIG. 4, some embodiments of a stent delivery system include a prosthesis (such as a stent) delivery and loader system 100 having an elongate element, which comprises a proximal end 110, tubular body 120, and distal end 130. The delivery system 100 can also include an extension 45 extending from side port 41 to an opening 42. Also illustrated are a valve body 40 and inner tube 30. In some embodiments, the prosthesis could be fully or partially biodegradable, as described, for example, in U.S. Pat. Pub. No. 2010/0016940 to Shokoohi et al., which is hereby incorporated by reference in its entirety. In some embodiments, a prosthesis delivery system includes a sterilizable disposable intraluminal medical device delivery system having a rigid, detachable, disposable, distal chamber 140 (DDDC) with a rigid distal section of the tip and flexible shaft and having one, two, or more lumens that can serve, for example, as guidewire and/or fluid injection ports. The chamber can house one or more prostheses 160 as illustrated.

In some embodiments, the prosthesis includes one, two, or more expandable elements such as balloons with one, two, or more radiopaque marker bands for proper positioning and placement under fluoroscopy. The balloon may be inflated to assist the physician or other end user with difficult procedures where a balloon may be incorporated in the procedure methodology (e.g., dilating a stenosis or dilation of an expandable medical device) per various clinical indications, requirements, or approaches to a type of treatment administered to an end user.

In some embodiments, the distal chamber, such as a detachable, disposable, distal chamber has an inner surface configured to maintain various co-efficients of friction and one, two, or more transition portions from a larger inner diameter to a reduced inner diameter. The inner surfaces may be treated in some cases with short-term or long-term surface activation methodologies such as, for example, plasma/corona treatment, vapor deposition, physical vapor deposition, chemical vapor deposition, sputtering, reactive sputtering, sintering, vacuum deposition, ion beam deposition, ion implantation, laser surface alloying, electroplating, chemical etching, physical etching, grit blasting, plasma spray coating, thermal spray coating, mechanical roughening, laser drilling, and metal sintering. Corona treatment can include applying an electrical discharge of considerable intensity to the surface of a given substrate, which may be constituted by a film or an extrusion with the purpose of increasing the active tension thereof and hence improving the capacity of anchorage of printing inks, adhesives, or coatings. Corona treatment is frequently applied to polyethylene, polypropylene, PVC, or polyester films but more in general can be used for all plastic materials and also some non-plastic materials, such as paper and aluminium.

The distal chamber can also include some form of surface treatment including vacuum deposition, bioactive, drug, hydrophilic, hydrophobic, and/or radioactive elements.

In some embodiments, the distal chamber while connected to the rest of the prosthesis delivery system in the sterile form may be unpackaged from a sterile vacuum sealed package comprising, for example a sterile Tyvek package where the system is stored and shipped under specific conditions. The distal chamber can include one, two, or more see-through, e.g., transparent windows or sections to allow observation of the prostheses transitioning from, for example, an expanded state to a compressed state and outer diameters changing as it moves through the distal chamber. Lubricious or other form of surface treatment, activations, or otherwise responsive characteristics may be adopted to make the multi-state transitional displacement on diameter and location manageable.

In some embodiments, the distal chamber may be assembled in such a manner as to serve as a container, resistance barrier, isolator and/or a carrier to a radioactive form of treatment technology, enhanced sterilization compatibility and containment for therapeutic solutions, and if desired for treatment precise positioning and placement under a specially programmed visualization fluoroscopic process software program. In some embodiments, the distal chamber may be mounted and attached during the final manufacturing operation and may be detached following moving the medical device proximally or distally out of the chamber as desired. In some embodiments, the distal chamber is connected and/or fitted to the tubular body of the delivery system by, for example, a compression fit mechanism, such as via a flange aligning with a flange of the distal end of the delivery system on an inner or outer surface.

In some embodiments, the delivery tool inserted into the body includes a rigid distal tip. The distal tip can also have a smooth and/or textured surface configured to cross lesions effectively and connected to an inner shaft as a part of coaxial shaft arrangement and located at the distal portion of the outer sheath possesses smooth surface texture and contains one, two, or more marker bands at various spaced-apart segments of the delivery system to assist with use and deployment of the medical devices. Some embodiments include such enhancements referred to as temporary or permanent surface activations which may partially or completely involve some surfaces of the system including the distal chamber and may include, for example, plasma treatment, corona treatment, hydrophilic, hydrophobic, and other surface treatments used for ease of insertion in to a body.

The distal end 130 can comprise a detachable chamber 140 having a zone including a lumen defining a first relatively large inner diameter, the first diameter sufficient to house therethrough a prosthesis, e.g., a stent 160 in less than its fully compressed configuration, such as an expanded configuration. The chamber 140 can be removably attached to the distal end of a tubular body 120 of a stent delivery system 100 according to some embodiments of the invention. The chamber 140 is detachable from more proximal portions of the stent delivery system 100 via, for example, a detachable joint 131, peel-away segment, perforations, reversible friction or compression fit, reversible locking components, or the like. The elongate tubular body also includes a segment 141 proximal to the detachable chamber 140, the segment 141 having a lumen having a second diameter smaller than that of the first diameter to carry a stent in its fully compressed state. In some embodiments, the segment 141 of the tubular body could have an inner diameter that could be no more than about 90%, 80%, 70%, 60%, 50%, 40%, 30%, 20%, or less of the inner diameter of the detachable chamber 140. Still referring to FIG. 4, the detachable chamber 140 can be advantageous in that it allows the stent 160 to be sterilized within the stent delivery system 100 in its expanded state, to decrease the likelihood of stent deformation that may occur when the stent 160 is sterilized in its fully compressed configuration, which may occur with conventional systems. Also shown in FIG. 4 is one, two, or more control wires 1210 having a distal end operably connected to and disconnectable from the stent 160 and a proximal end (not shown for clarity) operably connected to a control in which the physician can actuate to move the stent 160 proximally from the detachable chamber 140 into the smaller diameter tubular body 120 portion of the delivery system 100. Other mechanisms, either mechanical or others that do not require direct attachment to the prosthesis can also be used to move the stent, such as a source of vacuum or pressure. For example, a pressure source could be operably connected to the distal end of the distal chamber 140 and configured to move the prosthesis proximally into the tubular body 120 without damaging the prosthesis. As another example, a vacuum source could be connected to a vacuum or other proximal port on the tubular body 120 to move the prosthesis proximally into the tubular body 120 without damaging the prosthesis. The stent 160 can then be constrained in between inner tube 30 and the outer tube (e.g., smaller diameter tubular body 120 portion). The chamber 140 can also include a proximal transition segment as described, for example, below.

Figure 5:
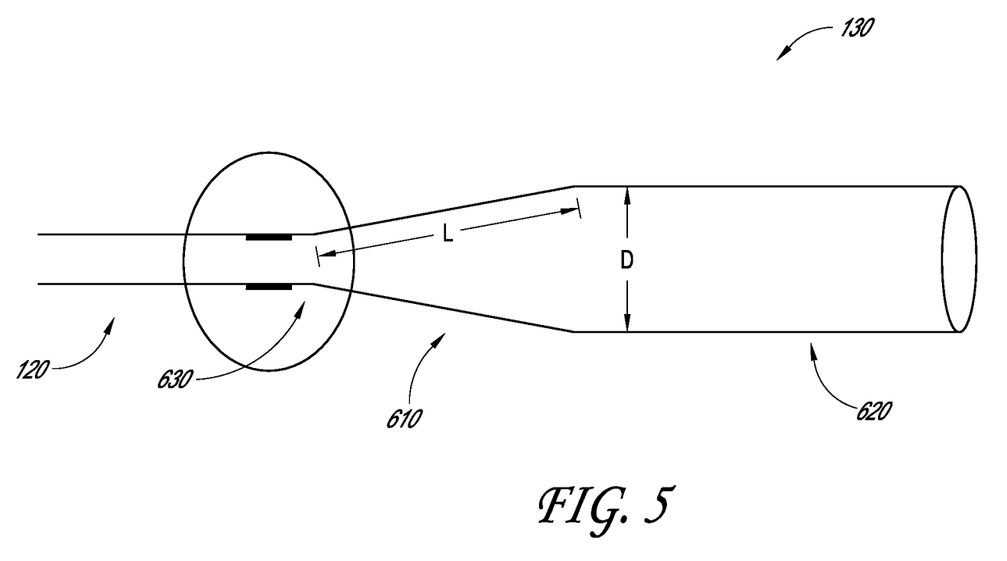
FIGS. 5-7 illustrate various configurations of a distal detachable chamber.
Figure 6:
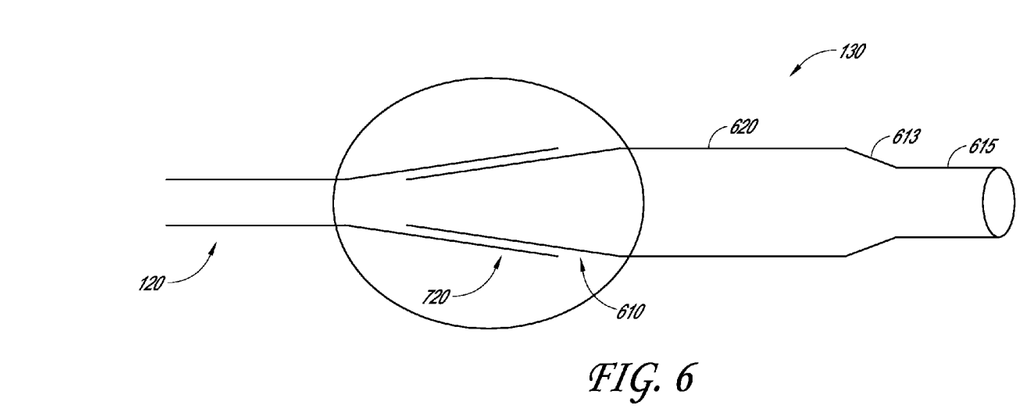
Figure 7:
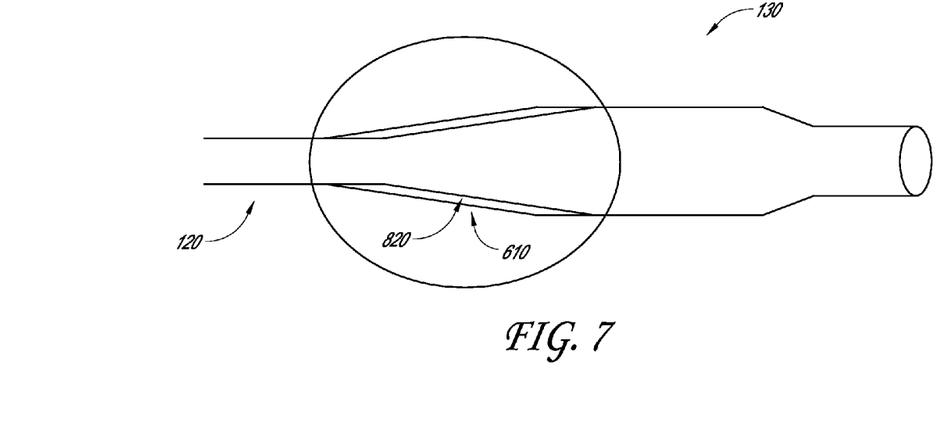

FIGS. 5-7 illustrate embodiments of possible shapes of the detachable chamber 140 and various ways in which the detachable chamber 140 can attach to the tubular body 120. In some embodiments, the detachable chamber 140 includes a first transition section 610 with a tapered or graduated cross sectional diameter (e.g., having a frustoconical cross-section), and a second section 620 with a constant or substantially constant, larger cross sectional diameter. In some embodiments, the first proximal transition section 610 is relatively more flexible than the second distal section 620 of the detachable chamber 140. Also illustrated is a third section or flange 630 proximal to first section 610 and second section 620 with a substantially constant smaller, or alternatively tapering cross sectional diameter. In FIGS. 5 and 6, shown are at least three different length segments referenced for each one of the three sections of the inner diameter of the distal chamber. In some embodiments, the axial length L of the first transition section 610 can have a dimension that is about, or more than about 1×, 1.25×, 1.5×, 1.75×, 2×, 2.25×, 2.5×, 3×, 4×, 5×, 6×, or more in dimension relative to the outer or inner diameter D of the second section 620 and creating a relatively axially long transitioning condition from a larger outer or inner diameter at one end of the transition section to a smaller outer or inner diameter at the other end of the transition section with a tapered inner shaft diameters connecting to the adjacent segments 630 and 620. The taper could be gradual, stepwise, or in some embodiments take the form of an accelerating or decelerating curve from distal to proximal. In some embodiments, the transition section could have a length that is between about 10 mm and about 80 mm, between about 10 mm and about 60 mm, between about 20 mm and about 40 mm, between about 10 mm and about 40 mm, or between about 20 mm to about 60 mm. FIG. 6 illustrates an embodiment of a distal detachable chamber 130 similar to that of FIG. 5, showing the relationship of the proximal-most segment 610 of the distal chamber and the distal-most segment 720 of the tubular body 120. As illustrated, the proximal-most transition segment 610 of the distal chamber has a generally increasing outer and/or inner diameter going from a proximal to a distal direction and the distal-most segment 720 of the tubular body 120 also has a generally increasing outer or inner diameter going from a proximal to a distal direction. Segments 720 and 610 (e.g., complementary fitting segments or flanges) can be configured to reversibly mate such that their sidewalls come into partially or completely overlapping contact or create a single plane when aligned side-by-side and attached, and the longitudinal axes of the sidewalls form an angle with respect to the longitudinal axes of the distal chamber and tubular body, respectively. In some embodiments, the detachable chamber has a inner diameter of between about 3 mm and about 27 mm in either the transition segment 610 or the second substantially constant segment 620 or between the two segments. In some embodiments, the angle can be between about 15 and 75 degrees, such as between about 30 and 60 degrees, such as about 45 degrees. As shown in FIGS. 6 and 7, the chamber 130 could also include an additional distal transition segment 613 having a taper opposite to that of proximal transition segment 610 (e.g., a decreasing outer or inner diameter from a proximal to distal direction) and a reduced diameter distal opening segment 615.

FIG. 7 illustrates an embodiment of a distal detachable chamber similar to that of FIG. 6, showing the relationship of the proximal-most segment or flange 610 of the distal chamber and the distal-most segment or flange 820 of the tubular body 120. However, in contrast to FIG. 6 showing the outer surface of the sidewall of the proximal-most segment 610 of the distal chamber being configured to mate with the inner surface of the sidewall of the distal-most segment of the tubular body 120, in FIG. 7 the inner surface of the sidewall of the proximal-most segment is configured to mate with the outer surface of the sidewall of the distal-most segment of the tubular body 120. Such an embodiment could be advantageous in certain circumstances, e.g., to prevent or reduce the risk of "bunching up" or damage to the prosthesis when the prosthesis moves proximally into the tubular body.

The cross sectional diameter of the second section 620 is, in some embodiments, substantially the same as the largest diameter of the first section 610. The second section 620 can be directly adjacent to the largest diameter of the first section 610, and the first 610 and second section 620 could be integrally or separately formed. In some embodiments (FIG. 5), the diameter at the base 630 of the detachable chamber is substantially the same as the diameter of the tubular body 120. Inner tube 30 on which the stent can be constrained on (akin to a mandrel) is not shown for clarity.

Referring to FIGS. 6-7, in some embodiments, the cross sectional diameter of the tubular body 120 increases at the distal end 720, 820 in order to accommodate the first section 610 of the detachable chamber 140. According to one embodiment (FIG. 6), the interior wall of the tubular body 140 contacts the exterior wall of the detachable chamber 140, at the distal end of the tubular body 720 and the first section 610 of the detachable chamber 140, such as via a lap joint. In another embodiment (FIG. 7), the exterior wall of the tubular body 140 contacts the interior wall of the detachable chamber 140, at the distal end of the tubular body 820 and the first section 610 of the detachable chamber 140, such as via the lap joint.

Figure 8:
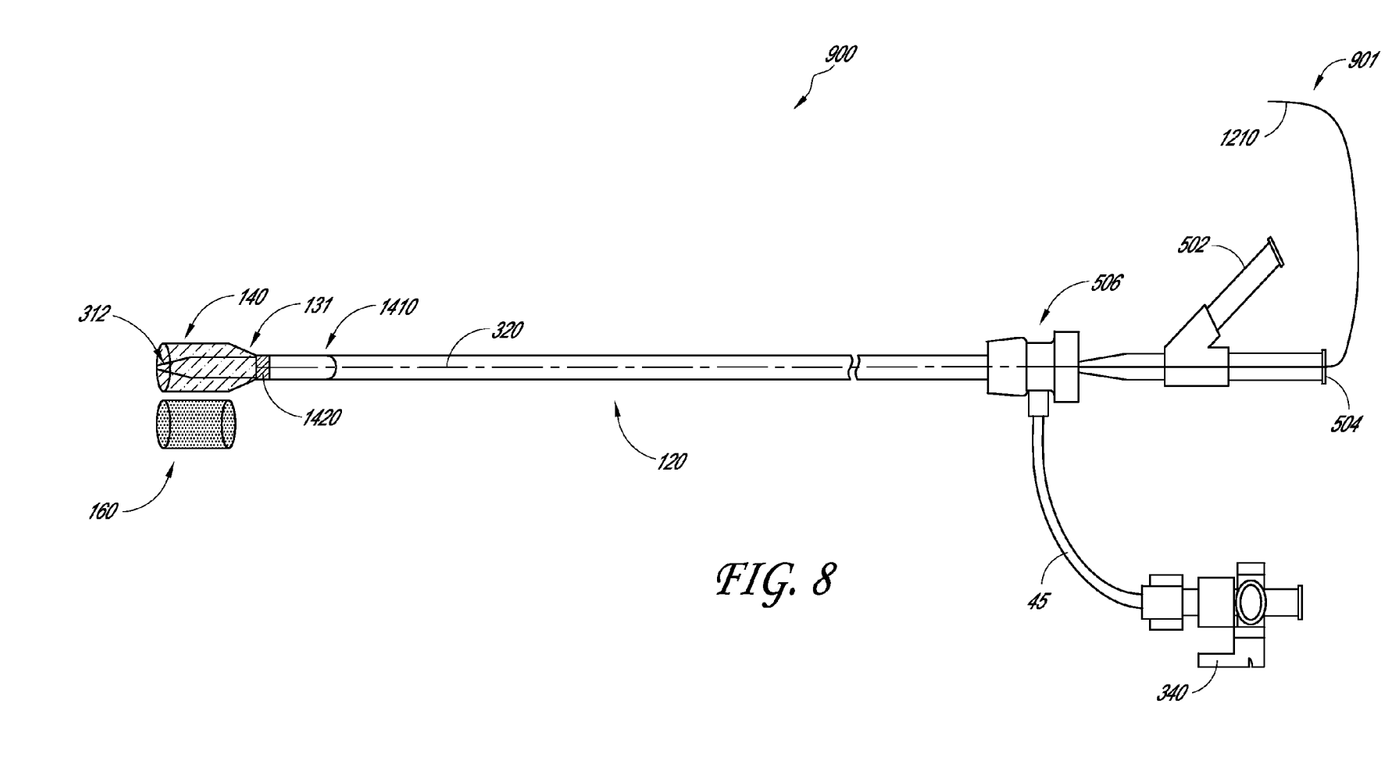
FIG. 8 illustrates schematically a coaxial stent delivery system that includes a distal detachable chamber, a proximal stent retraction feature, and an expandable member according to some embodiments of the invention.

FIG. 8 illustrates an embodiment of a coaxial stent delivery system 900 having proximal end 901 and distal end 902. Also illustrated near distal end 902 is the detachable chamber 140 with a detachable joint 131, peel-away element, or the like as previously described. Also shown is outer tube 120 running substantially along the axial length of the delivery system

900. The inner tube 310 (not shown) can comprise a distal tip 312 which extends through the lumen of the detachable chamber 140 as previously described. The detachable chamber 140 and distal tip 312 are configured so that a stent 160 can be loaded over the distal tip and through the lumen of the detachable chamber 140. The detachable chamber can include, for example, transition segments as described and illustrated in connection with FIGS. 5-7 above. Also illustrated is one, two or more expandable members (e.g., one or more balloons 1410) which can be disposed over the outer tube 120 or inner tube 310 in some embodiments for expansion or touch-up expansion of the prosthesis 160 once delivered to the target location within the body. Balloon 1410 is operably connected via inflation conduit (not shown) to port 502 at the proximal end. Also illustrated is port 504 which can be coaxial with the long axis of the delivery system 900, for loading of a guidewire, proximal retraction control wire 1210, snare, or the like as previously described, or other instruments; as well as check valve 340 and associated port for infusion, blood sampling, etc. connected via extension tubing 45 to proximal hub 506. Proximal hub 506 is also operably connected to ports 502, 504 as previously described.

Following sterilization of the stent 160 in its expanded configuration, the stent 160 can then be retracted proximally via a mechanical force such as a control wire 1210, snare, jaws, grasper, hooks, suture, or other means that are reversibly connectable to the implantable medical device including prostheses and/or a flat sheet or otherwise referred to as a part of a combination medical device and cause the prostheses to move proximally into the tubular body 120 where it assumes a fully compressed configuration for delivery. In some embodiments, a proximal control such as an adjustment knob operably connected to the control wire 1210 can be rotated in an appropriate direction, causing the control wire operably connected at its distal end to the stent 160 to pull the stent 160 in a proximal direction. In other embodiments, the same or a different control can effectuate release of the wire 1210 or other mechanism from the stent. In some embodiments, the stent 160 can be retracted proximally using a pressure gradient in addition to or instead of the mechanical force, such as via a proximal vacuum source and/or a distal media/pressure source configured to exert a blowing and or vacuum force, such as in a proximal direction. In some embodiments, compressed air, carbon dioxide, or other media can be used as part of the distal blowing force. The detachable chamber 140 is then removed, and the prosthesis delivery system 100 introduced into the desired body lumen.

Figure 9:
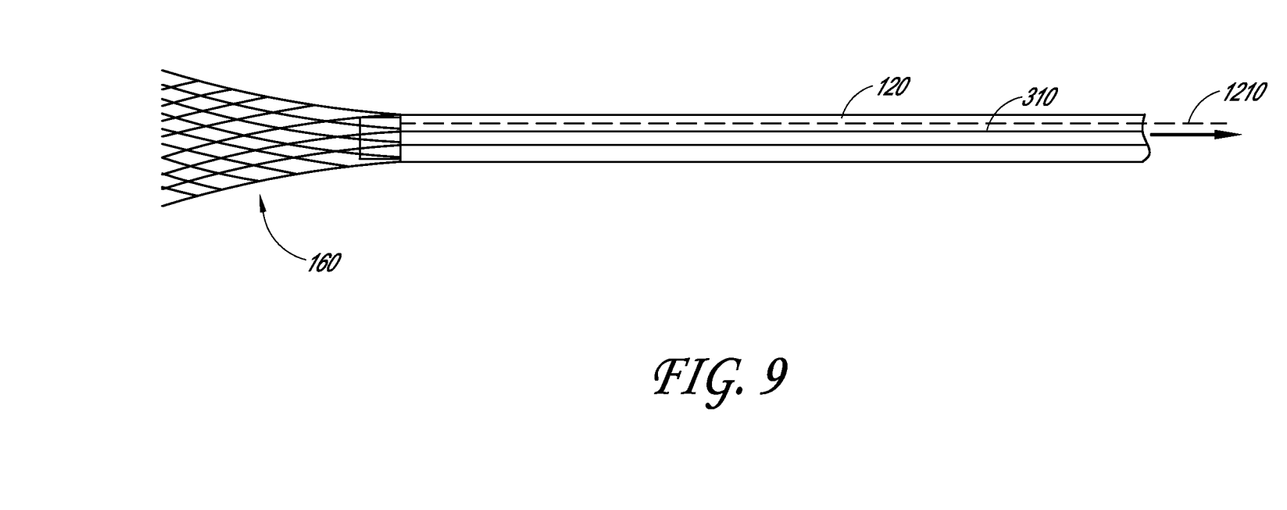
FIG. 9 illustrates schematically in action the proximal retraction feature of FIG. 8.
Figure 10:
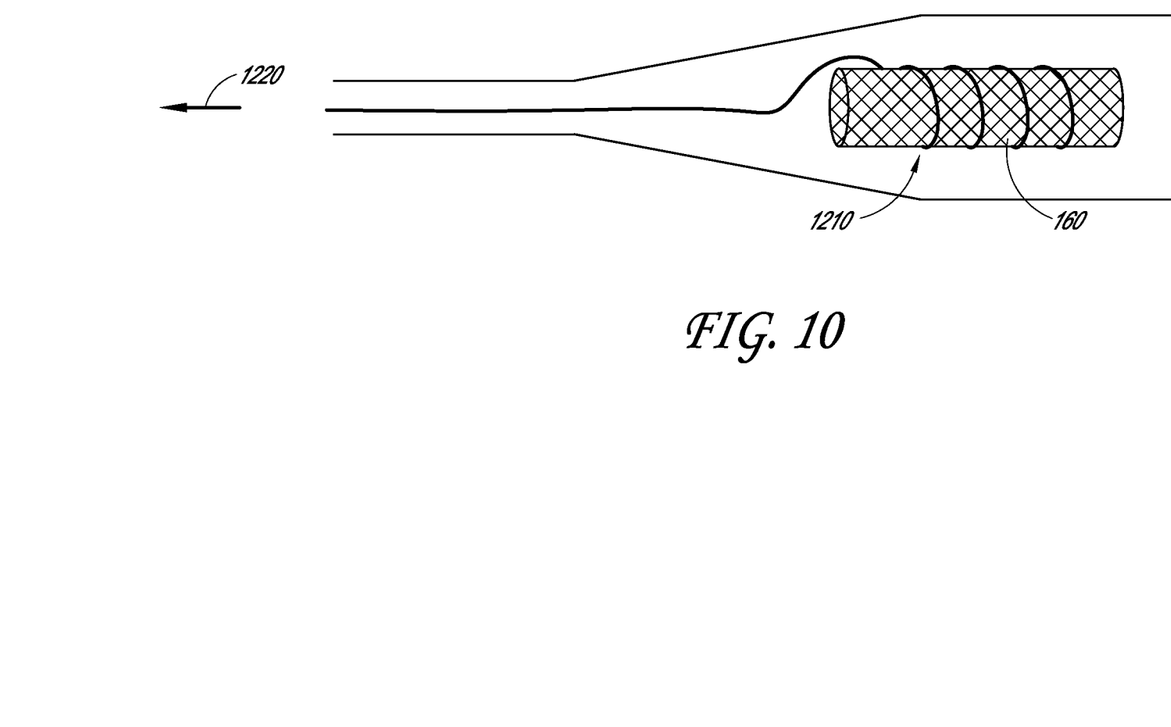
FIG. 10 schematically illustrates a proximal retraction feature that includes a control wire with one or more loops removably wrapped around the prosthesis.
Figure 11:
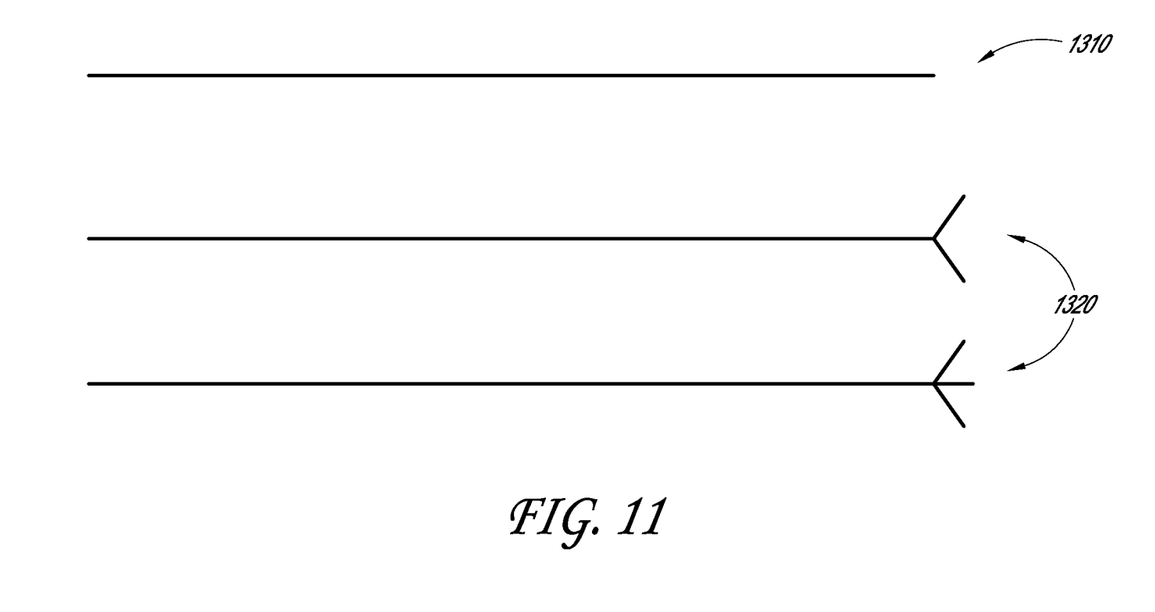
FIG. 11 schematically illustrates different embodiments in which a mechanical feature can removably connect to a prosthesis within a stent delivery system, according to some embodiments of the invention.

As illustrated by FIG. 9, retracting the stent 160 in an appropriate direction, such as proximally, e.g., via control wire 1210 transforms the stent 160 from a less than fully radially compressed configuration to a fully radially compressed configuration. The detachable chamber 140 is not shown in FIG. 11 for clarity. FIGS. 10-11 illustrate various embodiments of mechanisms for proximally retracting a drug eluting implantable medical device 160. A wire, string, ribbon, strip, suture, or the like, 1210 is removably attached to a stent 160 in its less than fully compressed configuration and housed inside the detachable chamber 140. In one embodiment, the wire 1210 is made of ePTFE or another suitable material. The wire 1210 can be wrapped helically or in any other suitable pattern around the stent 160. In some embodiments, the wire 1210 can be removably attached to the stent 160 through single strand connections 1310 or multiple strand connections 1310, or at 1, 2, 3, 4, 5 or more discrete points on the stent. The implantable medical prostheses 160 can be mechanically displaced or relocated to such position distal to or proximal to the distal section of the tip of the delivery system, while proximally retracted by applying a proximal force to the wire 1210. As the mechanical force is applied, the stent 160 assumes a compressed configuration in the tubular body 120, and the wire 1210 releases from the stent 160 the circular wrap, and/or loops through, and/or in & out of the struts, wherein some other embodiments hooks, jaws, and or other mechanisms can displace the implantable medical by release of grasper arms, electrolytic detachment, or other means.

In one embodiment, the combination medical device containing bioactive or radioactive eluting capabilities 160 is retracted proximally onto an inner tube 310 and into the lumen of an outer tube 320 as previously described. The detachable chamber 140 is then removed. The stent 160 assumes a fully compressed configuration and is prevented from expanding during delivery by the presence of the coaxially arranged outer tube 320. The distal end of the delivery system 300 can then deployed to the desired location in the body over a guidewire, for example, a stenosis in a coronary or a peripheral artery. The marker 11 on the distal end 322 of the outer tube 320 can be utilized to facilitate proper positioning. Relative movement of outer tube 320 with respect to inner tube 310, such as in a proximal direction can allow the stent 160 to self-expand.

Figure 12:
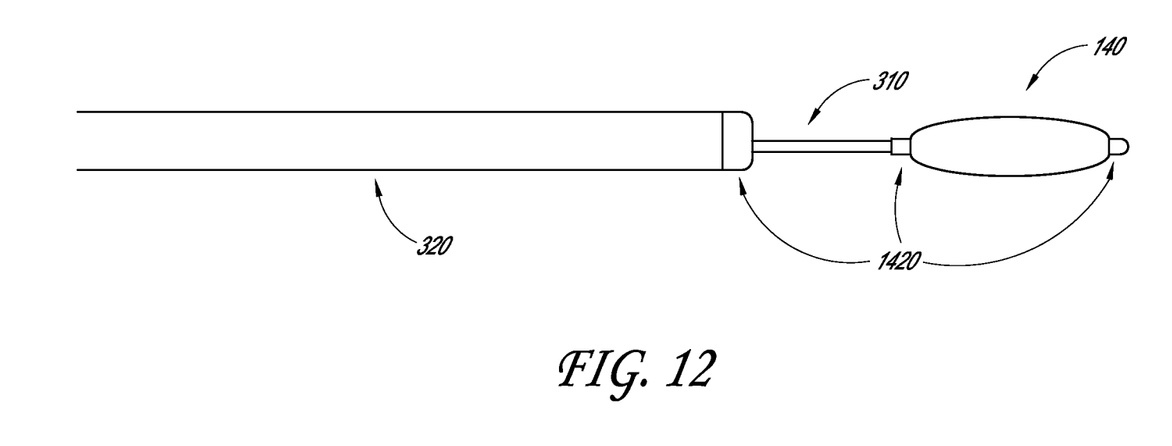
FIG. 12 schematically illustrates an expandable member and radiopaque markers as part of a stent delivery system, according to some embodiments of the invention.

Referring to FIG. 12, in some embodiments of the invention, the delivery system can include a radially expandable element, such as a balloon 1410 as previously described. The balloon 1410 is positioned over the distal end of an inner tube 310, with radiopaque markers 1420 placed on the inner tube 310 near both ends of the balloon 1410. The outer tube 320 is configured to house the balloon 1410 and inner tube 310 and can also have markers on one or more ends, and/or at a set distance away from the ends, such as 5 mm, 10 mm, 15 mm, 20 mm, etc. FIG. 12 illustrates the inner tube 310 and balloon 1410 extended out of the outer tube 320 for clarity. A stent 160 or other prosthesis can be proximally retracted over the balloon and into the lumen of the outer tube. During implantation, the radiopaque markers 1420 can be used to visualize the position of the stent 160 through fluoroscopy or other imaging modality.

Figure 13:
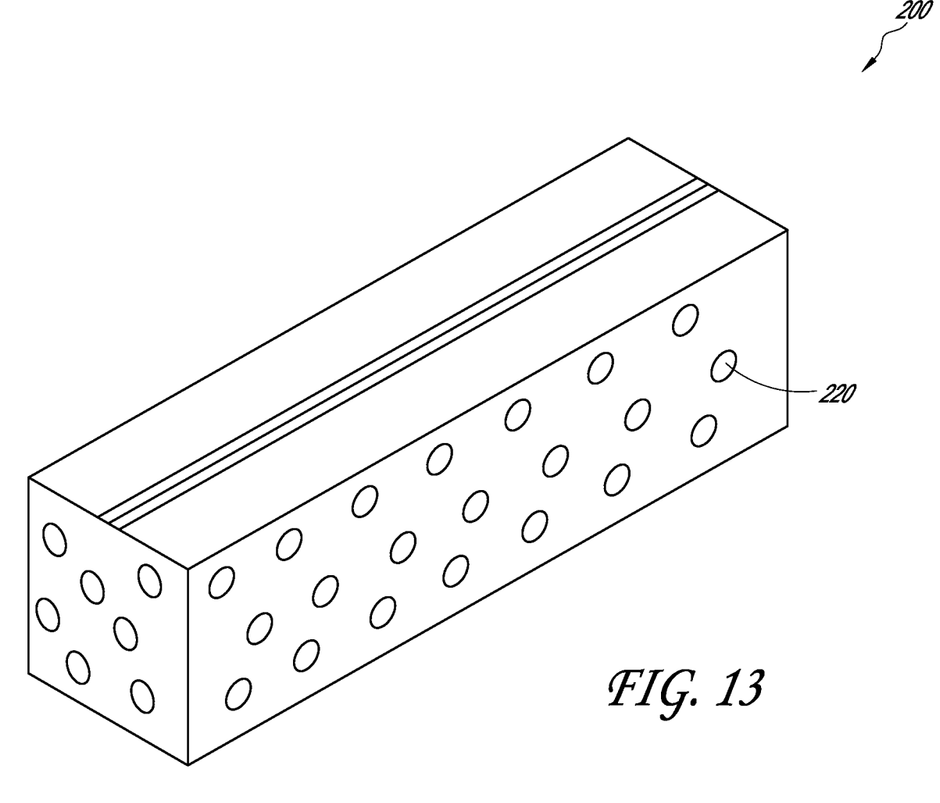
FIG. 13 illustrates an embodiment of a packaging housing for a stent delivery system.

As illustrated in FIG. 13, the prosthesis delivery system 100 can be packaged in a box 200 with pores or orifices 220 of the same or different sizes, to permit sterilization via, for example, a gas such as nitric oxide or other means. The prostheses and delivery system components as described herein can be sterilized by a variety of processes, including ethylene oxide (EtO) with a relatively short degassing cycle, radiation (gamma or e-beam) or heat (steam or dry) processes. Other relatively low temperature processes that can be used include vaporized hydrogen peroxide, hydrogen peroxide gas plasma, or ozone.

A relatively new sterilization process relies on oxides of nitrogen, and principally, nitrogen dioxide. Such a process can be useful, for example, for a combination device that includes a drug delivery characteristic. In the presence of oxygen (air), nitric oxide reacts to form reactive nitrogen species (RNS) including nitrogen dioxide ($NO_2$) and, to a much lesser concentration, its dimer, dinitrogen tetroxide ($N_2O_4$). Other transient species may be present at low concentrations (<1 ppm), including: nitrogen trioxide ($NO_3$), dinitrogen trioxide ($N_2O_3$), dinitrogen pentoxide ($N_2O_5$), and nitrous oxide ($N_2O$). In a sterilization chamber where NO is mixed with air, most of the NO reacts to form $NO_2$. The only other oxide of nitrogen that forms under these circumstances and is stable at concentrations higher than 1 ppm is $N_2O_4$, which exists in equilibrium with $NO_2$ and the concentration of which is determined by the $NO_2$ vapor pressure. If the air is humidified, $NO_2$ can be converted into nitric acid ($HONO_2$) at trace levels. Other and alternate sterilization may be utilized including but not limited to Ethylene oxide (EtO).

A recently developed sterilization process uses low concentrations (less than about 30, 25, 21, 20, 15, or less mg/L) of nitrogen dioxide gas in the presence of air and water vapor. The process is typically delivered at or near room temperature and consists of evacuation of air from the chamber, the introduction of the sterilant, and the addition of humidified air to a preset pressure, which is typically at or near ambient pressure. Depending on the physical design and packaging of the device to be sterilized, the sequence of: vacuum→sterilant injection→humid air injection may be repeated several times or the sequence can be changed. At the nitrogen dioxide concentrations used, and considering the operating temperature and pressure of the process, the $NO_2$ remains in the gas phase and acts as an ideal gas throughout the sterilization cycle.

It has been determined that in the gas sterilization process $NO_2$ is the key sterilizing agent. Other RNS may contribute in less-significant ways. Although the literature cites many other potential reactions, the specific environment established with the sterilization system limits the chemical species formed and the breadth of biological response. This limit allows the process to be focused and controlled.

Gas reactions that occur in the sterilization chamber are predictable and have been determined by calculation, computer modeling, and empirically. The sterilant gas concentration mixtures over time are predictable. The reaction rates and resulting concentrations of $NO_2$ and other oxides of nitrogen that result from the reaction of air and NO have been calculated. The starting concentration was set at 0.1% NO in air. NO reacts with oxygen in the air to create $NO_2$. The constant sum of NO and $NO_2$ indicates that these two molecules account for almost all of the nitrogen present. The calculations predict a rapid conversion of NO to $NO_2$ with only trace amounts of $N_2O_4$ due to the low $NO_2$ concentration. $NO_2$ is an effective sterilant at low concentrations, often between 6 and 12 mg/L, 8 and 10 mg/L and typically less than 21 mg/L, depending on the application. Therefore, relatively small containers of the $NO_2$ are required.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A prosthesis delivery system, comprising:
an elongate tubular body having a proximal end, tubular body, distal end, and a central lumen therethrough, the distal end comprising a distal chamber detachable from the remainder of the elongate tubular body, the distal chamber having a first rigid distal segment and a second flexible proximal transition segment, the first distal segment having an inner diameter, the inner diameter of the first distal segment being substantially constant and configured to house therethrough a prosthesis in a less than fully compressed configuration, the second proximal transition segment having an inner diameter that generally decreases from the distal end to the proximal end of the transition segment, the second proximal transition segment having an axial length that is at least 1.5× the inner diameter of the first distal segment, the tubular body having an inner diameter smaller than the inner diameter of the first distal segment of the chamber, and
a retrieval element configured to move the prosthesis proximally from the chamber, through the transition segment into the tubular body, thereby transforming the prosthesis from the less than fully compressed configuration when stored in the chamber to a fully compressed configuration.

2. The prosthesis delivery system of claim 1, wherein the second proximal transition segment has an axial length that is at least 2× the inner diameter of the first distal segment.

3. The prosthesis delivery system of claim 1, wherein the second proximal transition segment has an axial length that is at least 3× the inner diameter of the first distal segment.

4. The prosthesis delivery system of claim 1, wherein the inner diameter of the second proximal transition segment gradually decreases from its distal end to its proximal end.

5. The prosthesis delivery system of claim 1, wherein at least a portion of a sidewall defining the inner diameter of the first distal segment of the distal chamber comprises a corona surface treatment.

6. The prosthesis delivery system of claim 1, wherein at least a portion of a sidewall defining the inner diameter of the first distal segment of the distal chamber comprises a hydrophilic surface treatment.

7. The prosthesis delivery system of claim 1, wherein the distal chamber comprises an element selected from the group consisting of: a radioactive element, a drug, a stem cell, and a bioactive agent.

8. The prosthesis delivery system of claim 1, wherein the retrieval element comprises a control wire.

9. The prosthesis delivery system of claim 8, wherein the control wire comprises a suture.

10. The prosthesis delivery system of claim 1, wherein the retrieval element comprises a clamp.

11. The prosthesis delivery system of claim 1, wherein the retrieval element is configured to removably attach to the prosthesis.

12. The prosthesis delivery system of claim 1, wherein the retrieval element comprises a vacuum source operably connected to a proximal port on the tubular body.

13. The prosthesis delivery system of claim 1, wherein the retrieval element comprises a pressure source.

14. The prosthesis delivery system of claim 1, wherein the retrieval element comprises a control wire.

15. The prosthesis delivery system of claim 1, wherein the retrieval element is detachable from the tubular body via a friction fit.

16. The prosthesis delivery system of claim 1, wherein the retrieval element is detachable from the tubular body via a compression fit.

17. The prosthesis delivery system of claim 1, further comprising an expandable balloon proximate the distal end of the tubular body configured to radially expand the prosthesis.

18. The prosthesis delivery system of claim 17, further comprising a plurality of radiopaque marker elements positioned on the proximal end and a distal end of the balloon.

19. The prosthesis delivery system of claim 1, wherein at least a portion of the distal chamber has a see-through portion configured to allow an operator to visually gauge the relative position of the prosthesis within the delivery system.

20. The prosthesis delivery system of claim 1, wherein the tubular body comprises at least one fluid delivery port near the proximal end of the tubular body.

21. The prosthesis delivery system of claim 1, further comprising a guidewire configured to reside within the central lumen of the elongate tubular body.

22. The prosthesis delivery system of claim 1, wherein the chamber is disposable.

23. The prosthesis delivery system of claim 1, wherein the chamber comprises a first flange removably attached to a second flange of the tubular body, wherein the first flange and the second flange are angled with respect to a long axis of the chamber and a long axis of the tubular body.

24. The prosthesis delivery system of claim 23, wherein an inner surface of the first flange contacts an outer surface of the second flange.

25. The prosthesis delivery system of claim 23, wherein an outer surface of the first flange contacts an inner surface of the second flange.

26. A medical system comprising the prosthesis delivery system of claim 1, and an expandable prosthesis.

27. A method of delivering an expandable prosthesis, comprising:

providing a prosthesis delivery system having a detachable, disposable distal chamber removably attached at its proximal end to the distal end of a tubular body, the distal chamber having a first rigid distal segment and a second flexible proximal transition segment, the first distal segment having an inner diameter, the inner diameter of the first distal segment being substantially constant and configured to house therethrough the expandable prosthesis in a less than fully compressed configuration, the second proximal transition segment having an inner diameter that generally decreases from the distal end to the proximal end of the transition segment;

wherein the expandable prosthesis is stored in a first, relatively expanded state within the chamber; and transferring the expandable prosthesis from the chamber to the tubular body by using vacuum or pressure to move the expandable prosthesis proximally, transforming the prosthesis from the first relatively expanded state to a second relatively compressed state during the transfer.

28. A method of delivering an expandable prosthesis, comprising:

providing a prosthesis delivery system having a detachable, disposable distal chamber removably attached at its proximal end to the distal end of a tubular body, the chamber having a proximal flexible transition segment and a distal rigid segment having a substantially constant outer diameter, the transition segment having a proximal end and a distal end, the transition segment having an axial length, a first inner diameter at the proximal end and a second inner diameter at the distal end, the transition segment having a first inner diameter that is less than the second inner diameter of the transition segment, the transition segment having an axial length that is at least about 2× the outer diameter of the distal segment, wherein the expandable prosthesis is stored in a first, relatively expanded state within the chamber; and transferring the expandable prosthesis from the chamber to the tubular body to move the expandable prosthesis proximally, transforming the prosthesis from the first relatively expanded state to a second relatively compressed state during the transfer.

29. The method of claim 28, wherein transferring the prosthesis from the chamber to the tubular body comprises using vacuum.

30. The method of claim 28, wherein transferring the prosthesis from the chamber to the tubular body comprises using pressure.

31. The method of claim 28, wherein transferring the prosthesis from the chamber to the tubular body comprises moving a control wire removably connected to the prosthesis in a proximal direction.

32. The method of claim 28, further comprising delivering the prosthesis to a stenosis within a lumen of the body, and expanding the prosthesis to dilate the stenosis.

\* \* \* \* \*